United States Patent
Gazmuri et al.

(10) Patent No.: US 11,786,540 B2
(45) Date of Patent: Oct. 17, 2023

(54) GLIFLOZINS AND A METHOD FOR THEIR DELIVERY DURING RESUSCITATION FROM CARDIAC ARREST TO IMPROVE SURVIVAL OUTCOMES

(71) Applicants: Rosalind Franklin University of Medicine and Science, North Chicago, IL (US); The United States as Represented by The Department of Veterans Affairs (Washington, D.C.), Washington, DC (US)

(72) Inventors: Raúl J. Gazmuri, Chicago, IL (US); Jeejabai Radhakrishnan, Gurnee, IL (US); Salvatore Aiello, Inverness, IL (US)

(73) Assignees: Rosalind Franklin University of Medicine and Science, North Chicago, IL (US); The United States as Represented by the Department of Veterans Affairs, Washington, DC (US)

( * ) Notice: Subject to any disclaimer, the term of this patent is extended or adjusted under 35 U.S.C. 154(b) by 95 days.

(21) Appl. No.: 17/371,427

(22) Filed: Jul. 9, 2021

(65) Prior Publication Data

US 2022/0008446 A1 Jan. 13, 2022

Related U.S. Application Data

(60) Provisional application No. 63/050,670, filed on Jul. 10, 2020.

(51) Int. Cl.
*A61K 31/7048* (2006.01)
(52) U.S. Cl.
CPC ................................ *A61K 31/7048* (2013.01)
(58) Field of Classification Search
None
See application file for complete search history.

(56) References Cited

U.S. PATENT DOCUMENTS

| | | | |
|---|---|---|---|
| 8,133,860 B2 | 3/2012 | Gazmuri | |
| 2005/0209166 A1* | 9/2005 | Eckhardt | A61P 9/00 514/23 |

OTHER PUBLICATIONS

Andreado, Frontiers in Physiology, Dec. 2017, vol. 8, Article 1077. (Year: 2017).*
Baker, Basic Research in Cardiology (2019) 114:25. (Year: 2019).*
Helm, C. et al. "Adrenaline in cardiac arrest: Prefilled syringes are faster". Emergency Medicine Australia, 2015, pp. 312-316.
Villanueva, J.E. et al., "Empagliflozin Improves Cardiac Functional Recovery after Prolonged Cold Storage of Donor Hearts in an Isolated Working Rat Heart Model", the Journal of Heart and Lung Transplantation, Apr. 2020, vol. 39, No. 48, pp. S354-S355.
Zalewski, R. et al. "The use of prefilled adrenaline syringes improves cardiopulmonary resuscitation quality—high fidelity simulator-based study", Journal of Thoracic Disease, May 2020, vol. 12, No. 5, pp. 2105-2112.
Inzucchi, S.E. et al. "How Does Empagliflozin Reduce Cardiovascular Mortality? Insights From a Mediation Analysis of the MEPA-REG Outcome Trial", Diabetes Care, Feb. 2018, vol. 41, pp. 356-363.
Jevon, P. "The administration of drugs during resuscitation", Nursingtimes, Mar. 13, 2007, vol. 103, No. 11, pp. 26-27.
Papstylianou, A. et al. "Current Pharmacological Advances in the Treatment of Cardiac Arrest", Emergency Medicine International, 2012, vol. 2012, Article 815857, pp. 1-9.
KIPO, International Search Report and Written Opinion (PCT/US2021/041054), dated Nov. 1, 2021, pp. 1-11.

* cited by examiner

*Primary Examiner* — Layla D Berry
(74) *Attorney, Agent, or Firm* — Jared S. Manse; Greensfelder, Hemker & Gale, P.C.

(57) ABSTRACT

A method of performing cardiopulmonary resuscitation on a mammalian subject including the step of delivering an effective amount of a gliflozin solution during cardiac resuscitation through an intravenous or intraosseous route.

10 Claims, 6 Drawing Sheets

Table 1: Effects on Hemodynamic Function

| | BL | 15 | 30 | 60 | 90 | 120 | 150 | 180 | 210 | 240 |
|---|---|---|---|---|---|---|---|---|---|---|
| Heart Rate, from Left Ventricular Pressure Signal (bpm) [Tx = 0.367; Tx·Min = 0.707] | | | | | | | | | | |
| Control | 107 ± 5 | 126 ± 40 | 139 ± 21 | 138 ± 28 | 143 ± 34 | 162 ± 14 | 202 ± 61 | 203 ± 52 | 169 ± 121 | 173 ± 69 |
| EMPA | 91 ± 29 | 90 ± 20 | 80 ± 39 | 151 ± 14 | 154 ± 14 | 148 ± 17 | 147 ± 19 | 158 ± 25 | 158 ± 17 | 132 ± 27 |
| Ao, Mean (mmHg) [Tx = 0.331; Tx·Min = 0.034] | | | | | | | | | | |
| Control | 63 ± 1 | 39 ± 9 | 43 ± 10 | 44 ± 15 | 47 ± 9 | 48 ± 10 | 45 ± 6 | 38 ± 3 | 30 ± 10 | 25 ± 8 |
| EMPA | 66 ± 10 | 28 ± 3 | 32 ± 3 | 44 ± 9 | 50 ± 9 | 49 ± 8 | 48 ± 15 | 43 ± 12 | 48 ± 13* | 37 ± 10 |
| RA, Mean (mmHg) [Tx = 0.645; Tx·Min = 0.062] | | | | | | | | | | |
| Control | 10 ± 0 | 17 ± 9 | 13 ± 2 | 11 ± 2 | 10 ± 3 | 11 ± 2 | 10 ± 2 | 9 ± 2 | 12 ± 3 | 11 ± 4 |
| EMPA | 9 ± 2 | 20 ± 3 | 18 ± 4 | 11 ± 2 | 10 ± 2 | 9 ± 2 | 9 ± 1 | 8 ± 2 | 7 ± 1 | 8 ± 2 |
| PA, Mean (mmHg) [Tx = 0.853; Tx·Min = 0.934] | | | | | | | | | | |
| Control | 19 ± 6 | 24 ± 12 | 32 ± 16 | 23 ± 10 | 25 ± 14 | 33 ± 22 | 29 ± 18 | 25 ± 15 | 23 ± 11 | 21 ± 8 |
| EMPA | 21 ± 3 | 21 ± 10 | 28 ± 12 | 21 ± 9 | 26 ± 15 | 24 ± 13 | 24 ± 13 | 23 ± 12 | 28 ± 18 | 19 ± 9 |
| Cardiac Index (l/min·m⁻²) [Tx = 0.094; Tx·Min = 0.000] | | | | | | | | | | |
| Control | 3.6 ± 0.5 | 2.2 ± 1.3 | 2.3 ± 0.6 | 2.1 ± 0.8 | 2.2 ± 0.6 | 1.7 ± 1.1 | 2.1 ± 0.8 | 1.6 ± 1.0 | 0.9 ± 0.5 | 0.6 ± 0.0 |
| EMPA | 3.4 ± 0.2 | 0.7 ± 0.3* | 0.6 ± 0.0* | 2.4 ± 0.5 | 2.6 ± 0.6 | 2.8 ± 0.7 | 2.3 ± 1.3 | 2.5 ± 1.7 | 2.2 ± 0.5 | 2.3 ± 1.0* |
| Systemic Vascular Resistance Index (dynes·s·cm⁻⁵·m⁻²) [Tx = 0.525; Tx·Min = 0.064] | | | | | | | | | | |
| Control | 1195 ± 183 | 629 ± 417 | 1011 ± 171 | 1322 ± 438 | 1452 ± 507 | 2410 ± 1627 | 1499 ± 589 | 2039 ± 1456 | 1520 ± 339 | 1840 ± 1522 |
| EMPA | 1358 ± 299 | 1089 ± 557 | 2032 ± 991 | 1110 ± 242 | 1244 ± 187 | 1217 ± 497 | 1463 ± 490 | 1694 ± 1297 | 1467 ± 360 | 1221 ± 835 |
| $P_{ET}CO_2$ (mmHg) [Tx = 0.028; Tx·Min = 0.000] | | | | | | | | | | |
| Control | 36 ± 2 | 32 ± 13 | 33 ± 3 | 32 ± 6 | 30 ± 1 | 34 ± 2 | 31 ± 2 | 28 ± 4 | 17 ± 9 | 13 ± 9 |
| EMPA | 35 ± 2 | 8 ± 7† | 15 ± 2† | 38 ± 6 | 38 ± 7 | 36 ± 7 | 32 ± 11 | 29 ± 8 | 33 ± 5† | 26 ± 9* |
| Norepinephrine (μg/min) [Tx = 0.728; Tx·Min = 0.047] | | | | | | | | | | |
| Control | | 19.4 ± 0.3 | 38.9 ± 0.7 | 32.3 ± 10.9 | 28.4 ± 14.5 | 37.6 ± 1.8 | 38.9 ± 0.7 | 38.9 ± 0.7 | 38.9 ± 0.7 | 38.9 ± 0.7 |
| EMPA | | 15.6 ± 9.9 | 36.9 ± 10.3 | 15.7 ± 15.2 | 25.7 ± 22.8 | 15.8 ± 23.9 | 18.7 ± 22.3 | 18.7 ± 22.3 | 24.3 ± 22.1 | 22.9 ± 21.8 |

Shown are baseline followed by post-resuscitation data, with minutes from the start of high-flow extracorporeal circulation. Post-resuscitation measurements were obtained during brief interruptions of extracorporeal circulation (if still on) for the purpose of assessing native hemodynamic function. Each group included three animals each. EMPA = empagliflozin; Ao = aortic pressure; RA = right atrial pressure; PA = pulmonary artery pressure; $P_{ET}CO_2$, end-tidal $PCO_2$. Values are mean ± SD. The data was analyzed using a mixed-effect model showing (next to each variable name) the treatment effect (Tx) and the treatment interaction with time, treated as a continuous variable (Tx·Min). Also shown are differences between groups at specific times treating time as a discrete variable. *p ≤ 0.05, †p ≤ 0.01, ‡p ≤ 0.001.

Figure 6

Table 2: Effects on Left Ventricular Function

| | BL | 15 | 30 | 60 | 90 | 120 | 150 | 180 | 210 | 240 |
|---|---|---|---|---|---|---|---|---|---|---|
| Stroke Volume Index (ml/beat·m⁻²) [Tx = 0.456; Tx·Min = 0.015] | | | | | | | | | | |
| Control | 33.5 ± 4.8 | 16.1 ± 8.7 | 16.6 ± 3.0 | 15.0 ± 4.8 | 15.7 ± 5.6 | 10.2 ± 5.4 | 10.7 ± 4.6 | 7.8 ± 5.2 | 6.6 ± 3.6 | 3.9 ± 1.6 |
| EMPA | 39.1 ± 10.9 | 8.2 ± 3.6 | 8.4 ± 4.3 | 16.0 ± 5.4 | 17.3 ± 5.1 | 18.9 ± 4.3 | 15.2 ± 7.1 | 17.0 ± 12.4 | 14.1 ± 2.6 | 17.8 ± 8.2* |
| Left Ventricle Stroke Work Index (cJ) [Tx = 0.570; Tx·Min = 0.043] | | | | | | | | | | |
| Control | 29.5 ± 3.1 | 9.8 ± 6.8 | 10.5 ± 4.7 | 9.7 ± 6.2 | 11.6 ± 4.7 | 8.6 ± 3.1 | 8.1 ± 3.8 | 5.2 ± 4.2 | 2.6 ± 1.4 | 1.7 ± 1.3 |
| EMPA | 34.1 ± 6.9 | 3.3 ± 0.9 | 4.6 ± 2.2 | 10.1 ± 5.4 | 14.2 ± 5.8 | 16.1 ± 4.2 | 13.6 ± 10.6 | 13.5 ± 10.7 | 12.9 ± 5.3* | 9.5 ± 2.6 |
| LAD Coronary Artery Flow Relative to Baseline (%) [Tx = 0.467; Tx·Min = 0.001] | | | | | | | | | | |
| Control | 100 ± 0 | 123 ± 67 | 91 ± 60 | 102 ± 36 | 119 ± 12 | 168 ± 29 | 146 ± 26 | 137 ± 34 | 74 ± 66 | 47 ± 31 |
| EMPA | 100 ± 0 | 56 ± 32 | 84 ± 24 | 134 ± 64 | 209 ± 62* | 162 ± 37 | 177 ± 82 | 175 ± 31 | 226 ± 61† | 228 ± 109‡ |
| Coronary Vascular Resistance, (dyn·s·cm⁻⁵) [Tx = 0.635; Tx·Min = 0.543] | | | | | | | | | | |
| Control | 0.53 ± 0.01 | 0.14 ± 0.10 | 0.39 ± 0.16 | 0.32 ± 0.05 | 0.31 ± 0.10 | 0.22 ± 0.03 | 0.25 ± 0.01 | 0.21 ± 0.09 | 0.27 ± 0.05 | 0.28 ± 0.11 |
| EMPA | 0.57 ± 0.12 | 0.18 ± 0.08 | 0.17 ± 0.09 | 0.27 ± 0.07† | 0.21 ± 0.07 | 0.25 ± 0.08 | 0.23 ± 0.02 | 0.20 ± 0.08 | 0.19 ± 0.06 | 0.15 ± 0.11* |
| Sonometric Lateral Left Ventricular Wall Thickness, End-diastolic (mm) [Tx = 0.106; Tx·Min = 0.026] | | | | | | | | | | |
| Control | 6.0 ± 0.9 | 6.3 ± 0.9 | 7.1 ± 0.9 | 7.1 ± 1.0 | 7.0 ± 1.0 | 7.1 ± 0.9 | 7.1 ± 1.0 | 7.0 ± 0.9 | 7.1 ± 0.9 | 7.2 ± 0.9 |
| EMPA | 5.2 ± 0.9 | 4.7 ± 0.8 | 5.2 ± 1.3 | 5.1 ± 1.2* | 5.1 ± 1.2* | 5.1 ± 1.1* | 5.0 ± 1.1* | 5.0 ± 1.1* | 5.1 ± 1.2* | 5.0 ± 1.2* |
| Sonometric Lateral Left Ventricular Wall Thickness, Systolic (mm) [Tx = 0.355; Tx·Min = 0.019] | | | | | | | | | | |
| Control | 6.6 ± 0.9 | 6.6 ± 0.9 | 7.6 ± 1.3 | 7.4 ± 1.0 | 7.4 ± 1.0 | 7.7 ± 1.2 | 7.7 ± 1.4 | 7.6 ± 1.2 | 7.6 ± 1.1 | 7.7 ± 1.0 |
| EMPA | 6.2 ± 0.7 | 5.2 ± 0.5 | 5.7 ± 1.1 | 5.7 ± 1.1 | 5.8 ± 1.0 | 5.8 ± 0.9 | 5.7 ± 1.2* | 5.7 ± 1.1* | 5.7 ± 0.9* | 5.5 ± 1.1* |
| Sonometric Left Ventricular Shortening Fraction ([EDDiameter-ESDiameter]/EDDiameter) (%) [Tx = 0.864; Tx·Min = 0.135] | | | | | | | | | | |
| Control | 0.16 ± 0.03 | 0.12 ± 0.02 | 0.11 ± 0.01 | 0.10 ± 0.01 | 0.11 ± 0.03 | 0.13 ± 0.04 | 0.11 ± 0.04 | 0.10 ± 0.03 | 0.09 ± 0.02 | 0.12 ± 0.02 |
| EMPA | 0.15 ± 0.07 | 0.13 ± 0.01 | 0.15 ± 0.02 | 0.11 ± 0.03 | 0.16 ± 0.07 | 0.16 ± 0.11 | 0.17 ± 0.10 | 0.15 ± 0.11 | 0.15 ± 0.08 | 0.14 ± 0.08 |
| Tau (ms) [Tx = 0.898; Tx·Min = 0.046] | | | | | | | | | | |
| Control | 26.6 ± 4.2 | 45.9 ± 27.0 | 35.8 ± 7.3 | 31.2 ± 8.5 | 29.2 ± 9.1 | 41.8 ± 18.7 | 41.8 ± 10.9 | 51.4 ± 22.2 | 47.3 ± 5.2 | 52.2 ± 1.9 |
| EMPA | 29.1 ± 4.8 | 41.5 ± 20.2 | 33.8 ± 10.6 | 40.4 ± 3.9 | 31.4 ± 1.8 | 26.2 ± 3.3 | 29.9 ± 11.4 | 37.0 ± 13.0 | 32.1 ± 6.9 | 43.3 ± 9.3 |

Shown are baseline followed by post-resuscitation data, with minutes from the start of high-flow extracorporeal circulation. Post-resuscitation measurements were obtained during brief interruptions of extracorporeal circulation (if still on) for the purpose of assessing native left ventricular function. Each group included three animals each. EMPA = Empagliflozin, LAD = left anterior descending, EDDiameter = end-diastolic diameter, ESDiameter = end-systolic diameter, Tau = left ventricular relaxation time constant. Values are mean ± SD. The data was analyzed using a mixed-effect model showing (next to each variable name) the treatment effect (Tx) and the treatment interaction with time, treated as a continuous variable (Tx·Min). Also shown are differences between groups at specific times treating time as a discrete variable. *p ≤ 0.05; †p ≤ 0.01; ‡p ≤ 0.001.

Figure 7

GLIFLOZINS AND A METHOD FOR THEIR DELIVERY DURING RESUSCITATION FROM CARDIAC ARREST TO IMPROVE SURVIVAL OUTCOMES

CROSS-REFERENCE TO RELATED APPLICATIONS

This application claims priority to and the benefit of U.S. Provisional Patent Application Ser. No. 63/050,670 filed on Jul. 10, 2020 which is incorporated herein in its entirety by reference and made part hereof.

FEDERALLY SPONSORED RESEARCH OR DEVELOPMENT

N/A

FIELD OF THE INVENTION

The present invention relates generally to the use of gliflozins to facilitate resuscitation from cardiac arrest. Gliflozin are being used clinically in patient with diabetes mellitus for having an inhibitory effect on the sodium-glucose cotransporter type 2 (SGLT2). Administration of gliflozins during cardiac resuscitation acting through mechanisms different from SGLT2 inhibition improves resuscitation outcomes. Administration of gliflozins attenuates myocardial abnormalities caused by cardiac arrest and the resuscitation efforts. Gliflozins may be co-administered with any current or future drug used for cardiac resuscitation.

DESCRIPTION OF THE PRIOR ART

Studies have demonstrated that gliflozins, which are sodium-glucose cotransporter type 2 (SGLT2) inhibitors, significantly reduce major adverse cardiovascular events in subjects with type 2 diabetes mellitus.[1-3] Furthermore, gliflozins have been shown to also improve cardiac function and mitigate myocardial infarct size in metabolically normal animal models.[4,5] Empagliflozin (EMPA) is one of several gliflozins. A recent study known as Empagliflozin (EMPA), Cardiovascular Outcomes, and Mortality in Type 2 Diabetes (EMPA-REG OUTCOME) demonstrated that treatment with EMPA resulted in a 38% reduction in the relative risk of cardiovascular death and a 35% risk reduction of hospitalization for heart failure in patients with type 2 diabetes.[3] Assessment of the mechanisms responsible for the cardiovascular effect has shown in isolated cardiomyocytes that EMPA may exert its myocardial effects through inhibition of the sodium hydrogen exchanger 1 isoform (NHE-1) by occupying its $Na^+$-binding site.[6,7] A known NHE-1 inhibitor, zoniporide (ZNP), exerts similar effects but acts through a different site than EMPA.[7,8]

Our lab has extensively studied the effects of NHE-1 inhibitors to attenuate the injury to the myocardium that occurs after cardiac arrest secondary to the abrupt cessation of blood flow to the myocardium followed by the so-called reperfusion injury consequent to the delivery of oxygen in the blood to the globally ischemic myocardium during the resuscitation efforts.[9] For these studies, our group have used different animal models of cardiac arrest in which the mechanism to induce cardiac arrest has been VF. In one study, in a swine model of cardiac arrest, animals that received the NHE-1 inhibitor cariporide immediately before starting CPR experienced significant amelioration of myocardial wall thickening and reduction in left ventricular cavity size that is typically observed in control animals. The effect was associated with hemodynamically more effective CPR and improved resuscitation outcomes.[10]

In rat and swine models of ischemia-reperfusion, administration of gliflozins has resulted in reductions in infarct size up to 60% and attenuation of ventricular dysfunction during reperfusion as observed with canagliflozin.[11,12] However, gliflozins have not yet been investigated to assess whether they could elicit comparable beneficial effects on the myocardium during resuscitation from cardiac arrest as NHE-1 inhibitors do. Given that NHE-1 inhibitors are not currently available for clinical use, the ability of gliflozins to elicit NHE-1 inhibition—or NHE-1 inhibitory like activity—could be highly impactful to resuscitation from cardiac arrest. Therefore, we conducted preliminary experiments to assess whether EMPA could attenuate reperfusion injury in swine models of cardiac arrest produced by VF and elicit effects similar to NHE-1 inhibitors and thereby exert a beneficial effect for cardiac resuscitation.

For these studies, we first used an open-chest swine model of VF that enabled direct access to the heart to assess multiple parameters in a highly precise manner while resuscitation was performed using extracorporeal circulation (ECC) to simulate the low-flow states of cardiopulmonary resuscitation (CPR). We then used a closed-chest model that simulated the CPR technique currently used clinically for cardiac resuscitation.

In commonly assigned U.S. Pat. Nos. 8,067,366 and 8,133,860 disclose administering EPO during cardiac resuscitation to improve resuscitation outcomes.

SUMMARY OF THE INVENTION

A method of performing cardiopulmonary resuscitation on a mammalian subject including the step of delivering an effective amount of a gliflozin solution during cardiac resuscitation is described.

Other features and advantages of the invention will be apparent from the following specification taken in conjunction with the following Figures and Attachments.

BRIEF DESCRIPTION OF THE FIGURES

To understand the present invention, it will now be described by way of example, with reference to the accompanying attachment in which:

FIG. 6 shows a Table 1 of experimental results on effects of hemodynamic function.

FIG. 7 shows a Table 2 of experimental results on effects of left ventricular function.

DETAILED DESCRIPTION

Figure 1:
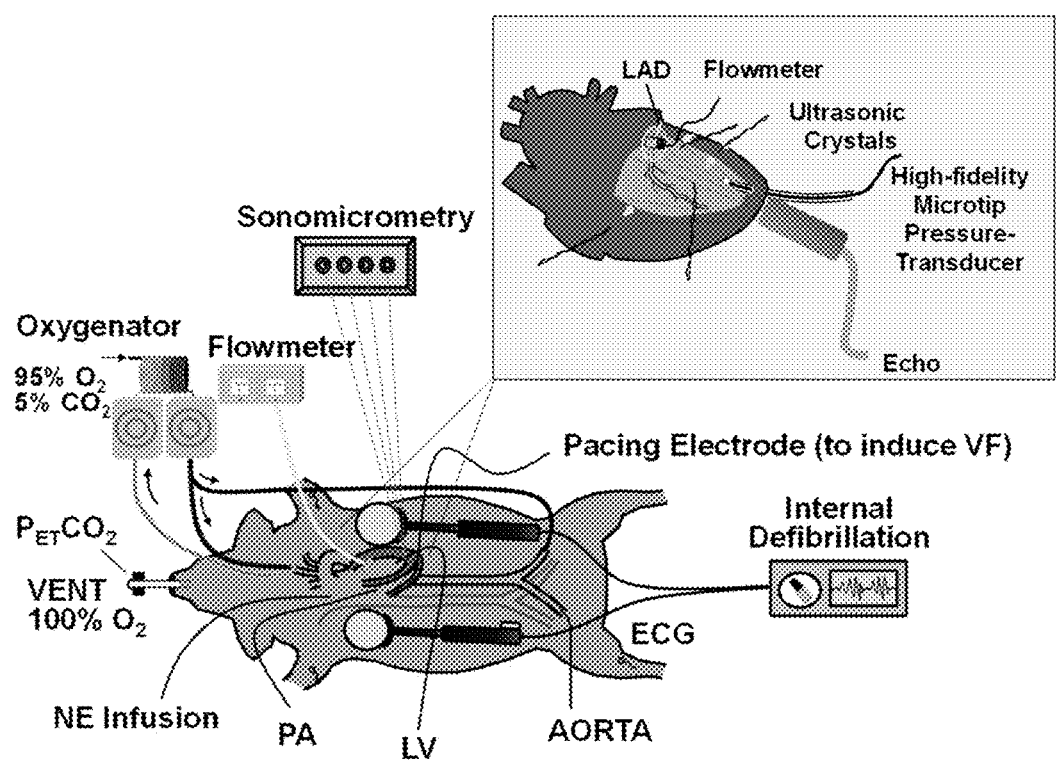
FIG. 1 is a schematic representation of surgical instrumentation used in an open-chest swine model.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

We hypothesized that bolus administration of EMPA, as a representative of gliflozins, during cardiac arrest prior to the initiation of CPR will attenuate reperfusion injury and elicit myocardial effects comparable to the effects elicited by NHE-1 inhibitors and thereby facilitate successful resuscitation from cardiac arrest.

Experiments in an Open-Chest Model

The studies were conducted in an open-chest swine model of electrically-induced VF and simulated CPR with controlled coronary blood flow (CBF) using extracorporeal circulation (ECC).[13,14] With a high degree of precision, the ECC model allowed subjecting the myocardium to low-flow reperfusion (as CPR does) after a period of ischemia during untreated VF (as it typically occurs in patients). The model reproduces adverse myocardial effects observed during CPR including increased myocardial wall thickness that is consistently ameliorated by NHE-1 inhibition. In addition, the model also reproduces post-resuscitation myocardial dysfunction which is also ameliorated by NHE-1 inhibition. In addition, the open-chest model allows for direct assessment of the myocardium via a micro-tip pressure transducer in the left ventricle to measure left ventricular pressure with high fidelity; a flow probe around the left anterior descending coronary artery to measure coronary blood flow as a surrogate of total myocardial blood flow; ultrasonic piezoelectric crystals to continuously measure the diameter (short-axis) and wall thickness of the left ventricle at the level of the mitral valve; and echocardiography to measure left ventricle volumes and wall thickness through a 4-chamber and 2-chamber views of the heart.

The maximum daily EMPA amount recommended clinically for patients is 25 mg orally.[3] Currently, there are no clinical guidelines for intravenous EMPA usage. We determined our dose based on previous animal and isolated heart models using different dosing strategies equivalent to a 25 mg oral dose in humans (0.69 µM blood concentration).[15-17] Exposure of isolated mice hearts to EMPA (1 µM) 18 minutes prior to myocardial ischemia and 25 minutes of ischemia, delayed the onset of myocardial contracture during ischemia.[18] In obese rats with diastolic dysfunction, a single EMPA injection (resulting in 8.68 µM blood concentration) improved isovolumic relaxation time after 30 minutes.[19]

Therefore, we chose an EMPA dose expected to achieve a blood concentration of 1 µM after initial blood volume distribution in our swine model of VF and resuscitation by ECC. For this purpose, a stock solution was first prepared by dissolving 90.2 mg of EMPA (Sigma, St. Louis, Mo., MW 450.92) in 10 ml of 100% DMSO to obtain a 20 mM solution. This stock solution was diluted in saline to 200 µM. Given an estimated blood volume of 2.5 L for a 40-kg pig, 2.5 µmoles (i.e., 12.5 ml of the 200 µM solution) were given in bolus dose to attain the target blood concentration of 1 µM EMPA after initial blood volume distribution. Yet, a substantially higher peak concentration was expected to be attained in the coronary circuit after the bolus injection and before blood volume distribution. Control pigs received 12.5 ml of 0.9% NaCl.

The bolus of EMPA or control solution was given at minute 9 of untreated VF through the venous port of the extracorporeal circuit. VF was maintained untreated for 10 minutes. ECC was then initiated and maintained for an additional 16 minutes. The ECC flow was titrated with the aid of a closed-loop system to generate and maintain a CBF of 25% of the baseline CBF, measured in the left anterior descending coronary artery.[20]

Given the preliminary nature of this study, we conducted 3 experiments each (EMPA and control) for a total of 6 experiments.

Methods

Animal Preparation

Six male domestic pigs (38.2 to 43.3 kg) were fasted overnight, sedated with ketamine hydrochloride (30 mg/kg intramuscular), and anesthetized with propofol (2 mg/kg through an ear vein). The trachea was intubated with a size-7.5 orotracheal tube and positive pressure ventilation initiated with 50% oxygen using a volume-controlled ventilator (840 Ventilator System, Nellcor Puritan Bennett, Boulder, Colo.) set to deliver 10 mL/kg at a peak flow of 60 L/min with an FiO2 of 0.5. The respiratory rate was adjusted to attain an end-tidal PCO2 (PETCO2) between 38 and 42 mmHg. Anesthesia was maintained using isoflurane (1.75%-2.75%). Rectal temperature was maintained between 37.5 and 38.5° C. with a servo-controlled water-circulated blanket (Blanketrol II, Cincinnati Sub-Zero, Cincinnati, Ohio). The ECG signal was obtained during spontaneous circulation through leads placed on the right forelimb, left forelimb, and left hindlimb. During VF, the ECG signal was obtained through pads from a biphasic waveform defibrillator (E series; ZOLL Medical Corporation, Chelmsford, Mass.) placed on the shaved sides of the chest along the midaxillary line.

A 7 F fluid-filled catheter was advanced from the right femoral artery into the descending thoracic aorta to measure aortic pressure. A 7 F thermodilution balloon-tipped catheter was advanced through the right external jugular vein into the pulmonary artery to measure cardiac output, right atrial pressure, pulmonary artery pressure, and pulmonary artery occlusive pressure (Swan-Ganz, Edwards Lifesciences, Irvine, Calif.). A 5 F pacing electrode was applied directly to the myocardial surface to induce VF. A 5 F fluid-filled catheter was advanced through the right internal jugular vein into the right atrium for norepinephrine (NE) infusion (FIG. 1).

For ECC, a 23 F cannula (Bio-Medicus®, Medtronic, Minneapolis, Minn.) was advanced through the surgically exposed left external jugular vein into the right atrium and used for blood removal. For blood return, two cannulas were used to achieve the desired extracorporeal blood flow; a 14 F cannula (Bio-Medicus) advanced into the surgically exposed left carotid artery and a 12 F cannula (Bio-Medicus) advanced into the surgically exposed left femoral artery.

A midline sternotomy was then performed. The chest was held open with retractors and the heart cradled on an open pericardium. A 5 F high-fidelity microtip pressure-transducer catheter (Millar, AD Instruments, Colorado Springs, Colo.) was inserted through the apex into the left ventricular cavity to measure ventricular pressures. Two pairs of 2-mm piezoelectric ultrasonic crystals (Sonometrics, London, Ontario, Canada) were embedded in the left ventricular myocardial wall to measure changes in ventricular dimensions. One pair was used to measure changes in left ventricular short-axis diameter embedding the crystals in the myocardial wall at the level of the papillary muscles, placing one crystal underneath the anterior endocardium and the other underneath the posterior endocardium. The second pair was used to measure changes in left ventricular lateral wall thickness at the level of the papillary muscles, placing one crystal underneath the endocardium and the other underneath the epicardium. A 4 mm flow probe (3PSB, Transonic Instruments Inc., Ithaca, N.Y.) was placed around the left anterior descending (LAD) coronary artery to measure coronary blood flow.

ECC Circuit

A heart-lung bypass roller pump (COBE Century Perfusion Pump, Medtronic, Minneapolis, Minn.), a hollow membrane oxygenator (SpiralGold, NovoSci, The Woodlands, Tex.), and biocompatible tubing ([3/8×3/32] [9.5 mm×2.4 mm] Intersept® Grade VI, Medtronic, Minneapolis, Minn.) were assembled to configure the ECC circuit. The system was primed with ~500 mL of 6% hetastarch in normal saline (Hespan, B, Braun Medical, Irvine, Calif.). Heparin (100 U/kg) was administered through the right atrial port of the pulmonary artery catheter. The extracorporeal circuit was then connected to the vascular cannulas. We used custom-designed LabVIEW-based closed-loop algorithms. One algorithm controlled the ECC pump speed to attain a pre-defined target coronary blood flow during VF corresponding to 25% of the baseline LAD blood flow (ECCLADflow-25%). Another algorithm controlled the ECC speed to attain a predefined mean aortic pressure (MAP) of 40 mmHg during the resuscitation and post-resuscitation phases (ECC-MAP-40 mmHg) and described in greater detail below. The system enabled a maximal pump speed of 250 RPM, corresponding to a maximum extracorporeal flow of approximately 3 l/min. During ECC, the oxygenator was supplied with a 95% O2 and 5% CO2 gas mixture at a constant rate of 3.5 l/min.[14]

Norepinephrine

Figure 2:
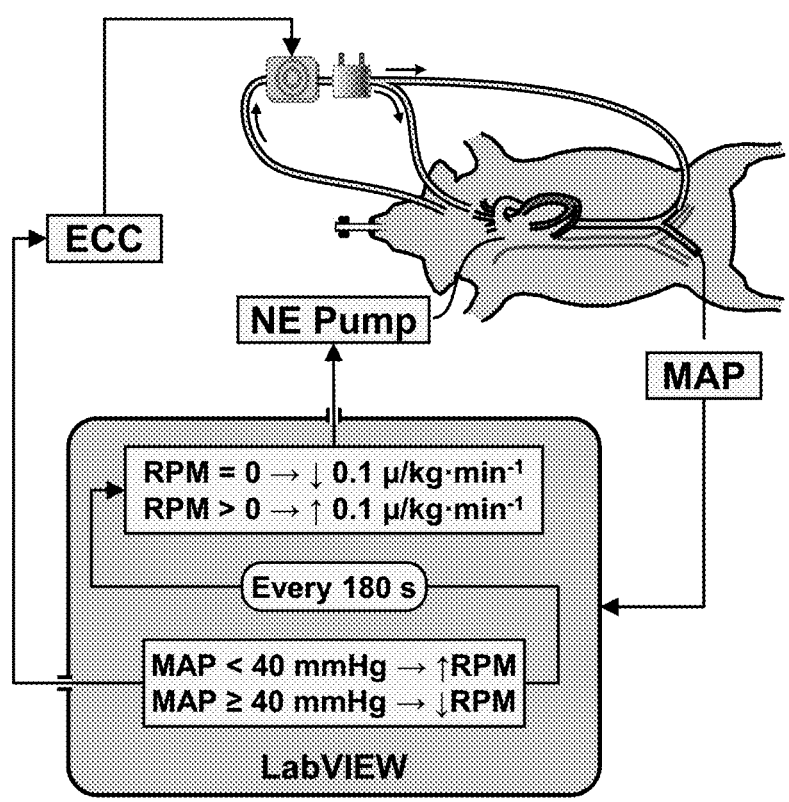
FIG. 2 is a schematic representation of an integrated closed-loop systems with algorithms for determining extracorporeal circulation circuit (ECC) flow (RPM) and norepinephrine (NE) dose based on mean arterial pressure (MAP) in an open-chest swine model.

Norepinephrine (NE) was infused into the right atrium using a syringe-pump (70-3005 PhD Ultra Injector, Harvard Apparatus, Washington, D.C.) at a rate ranging from 0 to 1 μg/kg·min−1 during the resuscitation and post-resuscitation phases. During the initial 5 minutes of ECCMAP-40 mmHg, before attempting defibrillation, the NE infusion was delivered at a fixed dose of 0.1 μg/kg·min−1. Thereafter, NE was delivery using a close-loop algorithm working in conjunction with the ECCMAP-40 mmHg algorithm to prevent the MAP from falling below 40 mmHg. Through this algorithm, the NE dose was responsive to the ECC speed requirement within the ECCMAP-40 mmHg algorithm. If the ECC speed was >0 RPM, the NE dose increased by increments of 0.1 μg/kg·min−1 every 180 seconds up to a maximum of 1 μg/kg·min−1. If the ECC speed was 0 RPM, the NE dose decreased by decrements of 0.1 μg/kg·min−1 every 180 seconds until 0 μg/kg·min−1 (FIG. 2).

Experimental Protocol

VF was induced by delivering an alternating current (1 to 10 mA) to the exposed right ventricular epicardium. Upon initiation of VF, positive-pressure ventilation and anesthesia were discontinued and the animal was left untreated for 10 minutes. EMPA or vehicle control was given to 3 pigs in each group as bolus dose at minute 9 of untreated VF through the venous port of the extracorporeal circuit. To ensure even mix between the extracorporeal Hespan prime solution and the animal's blood, the ECC was run for 2 minutes at 1 l/min. Thereafter, the ECCLADflow-25% algorithm was started and maintained for an additional 14 minutes, modeling the low-flow conditions of CPR.

After 26 minutes of VF with the last of 16 minutes receiving low-flow ECC, positive-pressure ventilation and anesthesia were resumed at baseline levels, and the ECC algorithm switched to ECCMAP-40 mmHg. After 5 minutes, defibrillation was attempted by delivery of a 10-J electrical shock to the myocardium using internal defibrillation paddles (E series Zoll Corp., Chelmsford, Mass.).[21] If VF persisted, additional shocks were delivered at 60-second intervals escalating the energy level by 10-J every 60 seconds up to a maximum of 50-J[21] In the described series, no animal required more than 30-J (i.e., 3 shocks).

Figure 3:
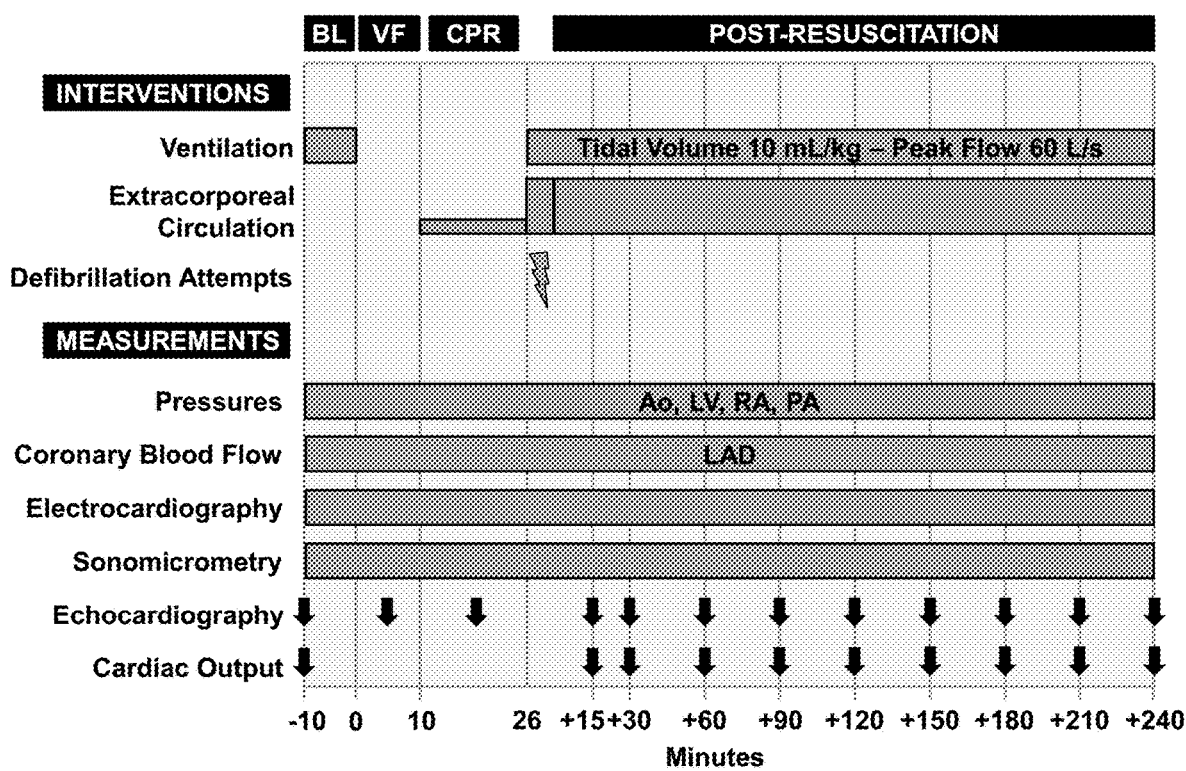
FIG. 3 is an experimental timeline from baseline (BL) through VF, CPR, and 240 min post-resuscitation. MAP=Mean arterial pressure; Ao=aortic; LV=left ventricle; RA=right atrium; PA=pulmonary artery; LAD=Left anterior descending coronary artery in an open-chest swine model.

After an electrically organized cardiac activity was established, ECCMAP-40 mmHg was continued working in conjunction with the NE algorithm until the end of the experiment (i.e., 240 minutes from the 40 mmHg MAP target set). Native cardiac and hemodynamic function was assessed by brief interruptions of the ECC flow (if still on) at minute-15, minute-30, and every 30 minutes thereafter until completion of 240 minutes (FIG. 3). At the end of 240 minutes post-resuscitation, animals were euthanized by a right atrial bolus injection of KCl (150 mg/kg).

Measurements

Hemodynamic Measurements

Thermodilution cardiac output was measured after bolus injection of 0.9% NaCl (10 mL) into the right atrium (Edwards Lifesciences Vigilance model, Irvine, Calif.) and normalized to body surface area using the Kelley equation (body surface area [m2]=0.073·body weight⅔ [kg].[22] Pressure-transducers attached to the various fluid-filled catheters were calibrated using a digital pressure gauge (DPG1000, Omega Engineering) and zeroed to mid-cavity level. The left ventricular microtip high-fidelity pressure-transducer catheter was zeroed in saline and calibrated using a pressure control unit (PCU-2000; Millar, Houston, Tex.) for digital reference values of 25 and 100 mmHg. The LAD coronary artery blood flow probe was calibrated once placed around the LAD coronary artery using reference values that would be displayed on a modular flowmeter system only if an adequate flow signal was present (TS402 Perivascular Flowmeter Module; Transonic, Ithaca, N.Y.). Analog measurements were sampled at 250 Hz and digitized using a 16-bit data acquisition board (AT-MIO-16XE-50; National Instruments, Austin, Tex.) and analyzed using custom-developed software (LabVIEW 6.0, National Instruments). The coronary perfusion pressure (CPP) during VF was defined as the difference between the MAP and mean right atrial pressures. LAD blood flow was normalized to baseline and reported as relative LAD blood flow (LADRF) to control for inter-animal variability in coronary anatomy and flow probe location. LADRF was used to calculate coronary vascular resistance (i.e., CPP divided by the mean LADRF).

Left Ventricular Functional Measurements

Pressures (by High-Fidelity Pressure Measurements)

From the left ventricular pressure signal, its systolic and diastolic pressures were determined; respectively corresponding to the peak pressure and the pressure immediately before the beginning of systole. In conjunction with the stroke volume index (SVI), determined by thermodilution (i.e., cardiac index divided by heart rate), the left ventricular stroke work index (LVSWI) was determined corresponding to the SVI times the difference between the systolic and the end-diastolic pressure and expressed in centijoules (cJ) by multiplying by 0.013332. In addition, the first derivative of the left ventricular pressure was used to determine the maximal rate of pressure increase (+dP/dtmax) and the maximal rate of pressure decrease (−dP/dtmax). Left ventricular relaxation was estimated by calculating tau from the descending portion of the ventricular pressure curve during isovolumic relaxation between the point of maximal pressure decline (−dP/dtmax) and 25% of the left ventricular end-systolic pressure. This portion of the left ventricular pressure typically follows a mono-exponential decay function and was fitted to the following function to calculate tau: $P(t)=Pi \cdot e-\tau/\tau$; where $P(t)$ is pressure as a function of time (t), Pi is the pressure at −dP/dtmax, and $\tau$ is Tau in msec.[23]

Dimensions (By Sonomicrometry)

Each pair of ultrasonic crystals was submerged in saline and calibrated before myocardial placement using digital reference values (0 and 50 mm) from the sonomicrometer box (UDG-1B1). The technique allowed measuring dimensions with a time and spatial resolution of 0.04 s and 15.9 μm. As described under animal preparation, the ultrasonic crystals were used to measure changes in the left ventricular anterior-posterior short-axis dimension and changes in left ventricular lateral wall thickness. The short axis dimension data was used to determine the shortening fraction (analogous to ejection fraction) of the left ventricle by taking the difference between end-diastolic diameter and end-systolic diameter divided by the end-diastolic diameter.

Volumes (By Echocardiography)

An ultrasound machine (Acuson Sequoia 512, Siemens, Germany) was used to measure left ventricular volumes. Ultrasound images were sequentially captured and stored as 5-second clips. The ultrasound probe was positioned perpendicular to the mitral valve to capture the parasternal long-axis view. Correct probe placement was confirmed when both ventricles were present, the pulmonary artery, and interventricular septum with the outflow track of the right ventricle were in view. End of systole and end of diastole were determined from the ultrasound machine ECG. The parasternal long-axis view was used to measure myocardial wall thickness and calculated from the stored clips using the caliper function to measure the interventricular wall thickness when prompted by the ultrasound machine cardiac calculation package.

Protocol for Left Ventricular Measurements

Assessment of left ventricular function and hemodynamic function at baseline and post-resuscitation were performed under normal sinus rhythm. During post-resuscitation, if ECC was required, the ECC pump speed and NE dose were recorded and the ECC transiently interrupted to assess native left ventricular and hemodynamic function. During this interruption, a right atrial bolus of normal saline was delivered to measure thermodilution cardiac output coincident with starting the ultrasound measurement followed by hemodynamic values measured immediately before resuming ECC. The duration of ECC interruption was typically between 120 to 240 seconds.

Statistical Analysis

The statistical analysis was performed using SPSS 26 (IBM Corp, Armonk, N.Y.). Continuous repeatedly measured variables were analyzed using a linear mixed effect model treating time as a continuous variable to assess main effects and interactions. Comparisons at each time point were obtained by treating each time point as a discrete moment mainly for descriptive reasons. A two-tailed $p<0.05$ was considered significant.

Results

Given the preliminary nature of this report, with only three experiments per group, a limited number of variables are reported describing the effects on hemodynamic and left ventricular function. Despite the small sample size, statistically significant differences were observed in favor of EMPA showing amelioration of post resuscitation myocardial dysfunction and improved hemodynamic function; effects of clinical relevance if translated.

Effects on hemodynamic function are shown on Table 1 (FIG. 6) and effects of left ventricular function on Table 2 (FIG. 7). At baseline, there were no differences between groups. In addition, there was no differences between the groups on myocardial changes during the resuscitation effort and the number of electrical shocks and corresponding cumulative energy required to terminate VF were the same in both groups (60-J). Post-resuscitation, one control animal had 4 episodes of recurrent VF between minutes 33 and 36, and in each instance, VF was successfully terminated after a 20-J shock.

Post-resuscitation, animals treated with EMPA exhibited a lower heart rate, but the differences were not statistically significant. Yet, animals treated with EMPA had a statistically significant higher MAP with a markedly higher cardiac index that was also statistically significant. The $P_{ET}CO_2$, which under conditions of constant metabolic activity, dead space, and minute ventilation reflects cardiac index, was also markedly higher in EMPA-treated animals. These effects of EMPA were observed while receiving lower doses of NE (FIG. 6, Table 1).

These favorable hemodynamic effects of EMPA were associated with higher stroke volume index, higher left ventricular stroke work index, and a substantially higher LAD blood flow, all statistically significant. The coronary vascular resistance was slightly lower in EMPA-treated animals, but the differences did not achieve statistical significance. Control animals developed progressive left ventricular wall thickening accompanied by increases in Tau, the relaxation time constant, all consistent with diastolic dysfunction. These effects were not observed in animals treated with EMPA (FIG. 7, Table 2).

Experiments in a Close-Chest Model

We used a swine model of VF and conventional closed-chest resuscitation with survival up to 240 minutes. We conducted 16 experiments in which 8 were randomized to receive EMPA and 8 to vehicle control given intravenously immediately before starting CPR.

Methods

Animal Preparation

Figure 4:
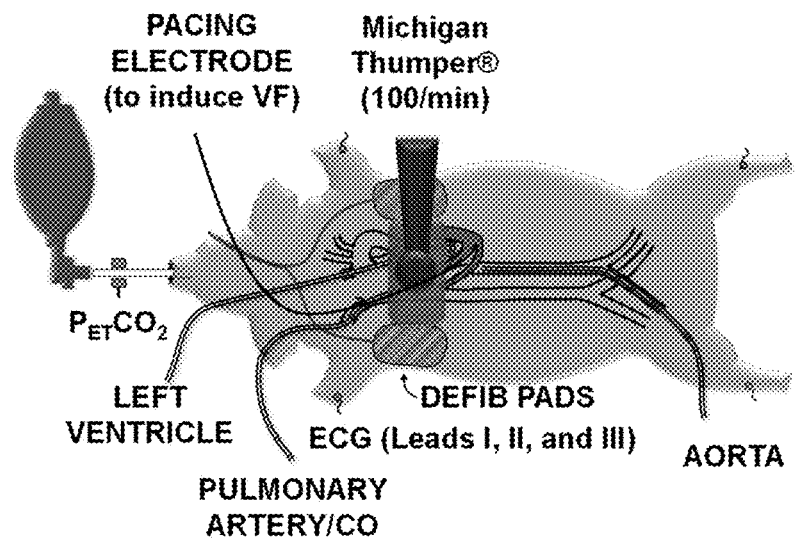
FIG. 4 is a schematic representation of instrumentation of a 35 kg to 40 kg pig for hemodynamic and electrocardiographic (ECG) monitoring for closed-chest resuscitation in a swine model.

Domestic pigs (35.2 to 39.6 kg) were sedated, anesthetized, intubated, and started on mechanical ventilation as for the experiments in the open-chest model. For blood sampling and measuring aortic pressures, a 6F dual lumen pressure monitoring catheter (Langston, Vascular Solutions) was advanced through the right femoral artery past the bifurcation and into the descending thoracic aorta. For measuring left ventricular pressures, a 7F fluid-filled pigtail catheter (Langston, Vascular Solutions) was advanced through the surgically exposed right carotid artery and into the left ventricle. For blood sampling and for measuring core temperature, cardiac output by thermodilution technique, and pressures in the right atrium and pulmonary artery, a balloon-tipped pulmonary artery catheter (Swan-Ganz, Edwards Lifesciences, Irvine, Calif.) was advanced through the right external jugular vein and into the pulmonary artery. For induction of VF, a 5F pacing electrode was advanced through the right internal jugular vein into the right ventricle (FIG. 4).

Experimental Protocol

VF was induced by delivering an alternating current (1-10 mA) to the right ventricular endocardium and left untreated without ventilation for 10 minutes. At the end of untreated VF, chest compressions were started using a mechanical compressor (Michigan Thumper Model 1007, Grand Rapids, Mich.) set to compress the chest at a rate of 100 per minute with its depth titrated attempting to generate an aortic diastolic pressure of at least 25 mmHg but without exceeding a maximum compression depth of 5 cm. Ventilation with 100% oxygen was delivered using a 350-ml self-inflating pediatric bag (Lifesaver Resuscitation Bags; Teleflex Medical, N.C.). Compressions and ventilations were delivered sequentially as recommended when the airway is un-protected. Accordingly, 30 chest compressions were delivered in 18 seconds followed by 2 breaths during a 6 second compression pause. Electrical shocks were delivered through the chest pads using a biphasic waveform defibrillator (R series Zoll Corp.) with the energy set at 200-J. Shocks were delivered guided by the likelihood of successful resuscitation using an algorithm developed by us based on real-time monitoring of the VF waveform in the frequency domain known as amplitude spectral area (AMSA).[24] Epinephrine (1 mg-bolus dose; 1 ml) was delivered through the pulmonary artery catheter into the right atrium and the line flushed with 10 ml of 0.9% NaCl. The timing of epinephrine delivery was based on an AMSA advisory criterion avoiding delivery if AMSA predicted a high likelihood of shock success within the ensuing 120 seconds, with a minimum interval between doses of 240 seconds. The purpose of AMSA advisory criteria was to minimize administration of epinephrine—given its known adverse post-resuscitation effects—if not required for successful resuscitation.[25,26] Animals that achieved ROSC received 0.9% NaCl (30 ml/kg) at the maximum pump rate (999 ml/h) and were monitored for up to 240 minutes, euthanizing those that survived by delivering a right atrial bolus of KCl (150 mg/kg).

For these experiments we used a higher EMPA dose corresponding to 0.5 mg/kg. In the open-chest model described above we used an EMPA dose of 0.028 mg/kg (intended to achieve a blood concentration of 1 µM (0.045092 mg/di) after initial blood volume distribution. Given that previous work with EMPA had not shown adverse effect of a higher dose corresponding to 0.5 mg/kg,[17] we decided to use this dose for the current experiments, expected to yield an estimated blood concentration of 17.8 µM (0.8026 mg/dl) after blood volume distribution.

For this purpose, a stock solution was prepared by dissolving 90.2 mg of EMPA (Sigma, St. Louis, Mo., MW 450.92) in 8 ml of 100% DMSO to obtain a 250 mM solution. This stock solution was diluted in saline to 5 mM. Given an estimated blood volume of 2.5 L for a 40-kg pig, 44.64 µmoles (i.e., 8.9 ml of the 5 mM solution) of EMPA was given in bolus dose into the right atrium immediately before starting CPR to attain the target blood concentration of 17.8 µM (0.8026 mg/di) after initial blood volume distribution. In control experiments, the same volume of 100% DMSO saline was used.

Statistical Analysis

The statistical analysis was performed using SPSS 26 (IBM Corp, Armonk, N.Y.). Continuous repeatedly measured variables were analyzed using a linear mixed effect model treating time as a continuous variable to assess main effects and interactions. A two-tailed $p<0.05$ was considered significant.

Results

Figure 5:
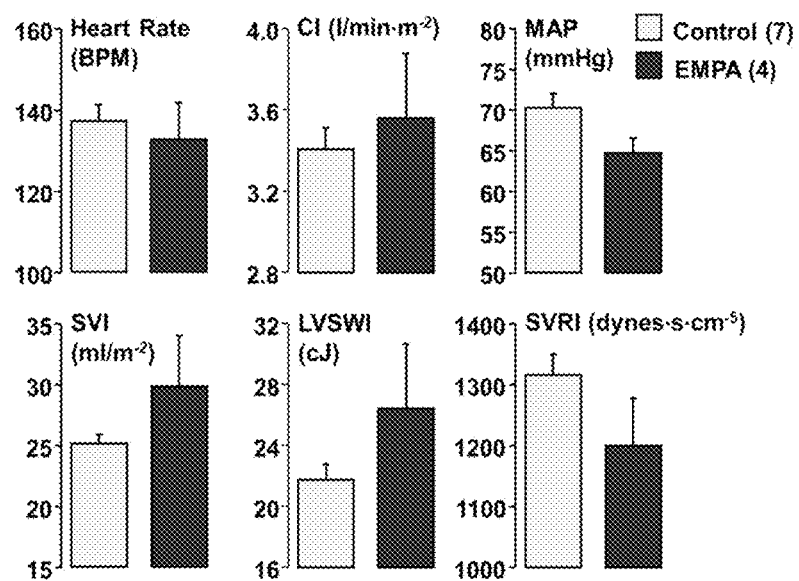
FIG. 5 is a series of bar graphs showing CI=cardiac index, MAP=mean arterial pressure, SVI=stroke volume index, LVSWI=left ventricular stroke work index, SVRI—systemic vascular resistance index. The measurements represent the average of 3 measurements obtained at 120-, 180-, and 240-minutes post-resuscitation (mean±SEM).

Relative to its comparator (n=8), administration of empagliflozin (n=8) was associated during CPR with a higher end-tidal $PCO_2$ (36±7 vs 29±7 mmHg) and a blunted pressor response to epinephrine that precluded ROSC in 4 animals (refractory VF). Post-resuscitation, the data was consistent with our earlier observations supporting a myocardial protective effect of empagliflozin resulting in a higher cardiac index, higher stroke volume index, and higher left ventricular stroke work index (FIG. 5). Also, and consistent with a vasodilatory effect, the mean arterial pressure and the systemic vascular resistance were lower (FIG. 5), and also the pulmonary vascular resistance (not shown). The findings of these additional preliminary experiments, though statistically underpowered, were consistent with our earlier findings also showing improved post-resuscitation myocardial function. Yet, the closed-chest experiments also showed concomitant systemic vasodilation, which could be beneficial during resuscitation enabling higher blood flow to be generated by chest compression and also beneficial post-resuscitation at the organ level (maintaining microcirculatory blood flow).[27,28]

Discussion

In these studies, no myocardial differences were observed during the resuscitation phase between EMPA and control treated animals. However, during the post-resuscitation phase, animals treated with EMPA had better myocardial and hemodynamic function. The favorable hemodynamic effects were observed at lower NE doses in the open-chest series and attributed to better post-resuscitation left ventricular systolic and diastolic function, evidenced by a higher left ventricular stroke work index accompanied by less wall thickening and faster relaxation. In addition, and consistent with the improved left ventricular stroke work, the coronary blood flow was also higher in the EMPA-treated animals in the open-chest series.

Studies have demonstrated that gliflozins significantly reduce major adverse cardiovascular events in patients with type 2 diabetes mellitus.[2,3] Moreover, gliflozins have been shown in metabolically normal animal models to improve cardiac function and mitigate myocardial infarct size.[12,24] For example, in an isolated Lagendorff-perfused mouse hearts model of global ischemia and reperfusion, EMPA delayed ischemic contracture and reduced infarct size.[18] Cariporide, an NHE-1 inhibitor, also elicited similar effects. Moreover, in a rat model of coronary occlusion and reperfusion, canagliflozin treatment reduced infarct size and ameliorated systolic and diastolic dysfunction.[11] In addition, in a swine model of coronary occlusion and reperfusion, oral administration of canagliflozin 24 hours before the experiments and again at 2 hours before coronary occlusion resulted in better stroke volume and cardiac output after reperfusion.[12]

In studies assessing the mechanisms responsible for the cardiovascular effects of gliflozins, EMPA in isolated cardiomyocytes exerted effect similar to NHE-1 inhibition evidence by reductions in cytosolic sodium and cytosolic calcium.[6,7] It is well-established that myocardial NHE-1 is activated during ischemia leading to sodium-induced cytosolic and mitochondrial calcium overload. We have well-established that NHE-1 inhibitors exert a beneficial myocardial effect during cardiac resuscitation using rat and swine models of cardiac arrest and resuscitation.[9] The beneficial effects are characterized by amelioration of left ventricular wall thickening and preservation of left ventricular cavity size (enabling hemodynamically more effective chest compressions) and by improved post-resuscitation myocardial function (enabling better hemodynamic function).[10]

These effects are attributed mechanistically to reductions in sodium-driven cytosolic and mitochondrial calcium overload resulting in preservation of mitochondrial bioenergetic function. The beneficial mitochondrial effects are also evidenced by lower plasma levels of cytochrome c inversely proportional to left ventricular function.[25] Cytochrome c is a mitochondrial protein that is released when mitochondrial injury occurs. The activation of NHE-1 likely persists for several hours post-resuscitation creating a relatively long therapeutic window for amelioration of myocardial injury via NHE-1 inhibition.[26]

The mechanisms by which gliflozins might inhibit NHE-1 are not well understood. As discussed earlier, a study in isolated mouse cardiomyocytes showed that EMPA exerted NHE-1 inhibition by occupying its Na+-binding site.[6,7] Other studies, however, suggest indirect mechanisms because the rate of intracellular pH recovery, a direct measure of NHE-1 activity, in various cell lines, was not blunted by exposure to gliflozins.[27] Using AP-1 cells transfected with wild-type NHE-1 and human IPSc-derived cardiomyocytes, canagliflozin treatment did not result in a complete halt of pH recovery whereas the NHE-1 inhibitor cariporide did.[27] Likewise, in studies by us using H9c2 cells, treatment with EMPA did not result in a complete halt of pH recovery as observed with the NHE-1 inhibitor zoniporide. So far, to the best of our knowledge the only study that showed reduction in the rate of pH recovery upon treatment with gliflozins, was the study cited above in isolated mouse cardiomyocytes.[7] Although, differences in NHE-1 expression among different cell types used in different studies could explain the contradictory results, another possibility is the existence of an indirect mechanism of NHE-1 inhibition by gliflozins not captured during cell assays of short duration. It is well known that NHE-1 activity is regulated by various kinases.[9] One important player is calcium/calmodulin-dependent kinase II (CaMKII).[28,29] CaMKII has been reported to activate and increase NHE-1 activity by signaling through its intracellular domain. Isolated cardiomyocytes exposed to EMPA for 24 hours showed a reduction in CaMKII activity and CaMKII-dependent sarcoplasmic reticulum calcium leak with concomitant reductions in cytosolic sodium and calcium levels.[28] This suggests that the reduction of CaMKII activity by EMPA led to reductions in NHE-1 activity. Of clinical relevance, understanding the mechanisms involved in the beneficial effect of EMPA may provide an opportunity to minimize the known detrimental effect of epinephrine during cardiac resuscitation.[30,31]

Conclusions

In these preliminary studies, animals treated with EMPA demonstrated less left ventricular dysfunction after resuscitation from cardiac arrest leading to better post-resuscitation hemodynamic function. Although the mechanisms through which EMPA exerted these beneficial effects are incompletely understood, the observed effects are relevant to clinical resuscitation. Moreover, because of similar effects by other gliflozins on ischemia and reperfusion injury, it is likely that the effects observed on cardiac resuscitation is a class effect that could be elicited by any of the other currently available gliflozins. Given the clinical availability of EMPA, and other gliflozins, repurposing these drugs could markedly enhance the translation of our laboratory observations to clinical resuscitation from cardiac arrest, exerting a profound impact in the field of resuscitation in need of substantial improvement from the currently disappointing survival outcomes.

Method of Treating Human Patients in Cardiac Arrest

Based on these studies, we have developed a method for treating mammalian subjects including human patients in cardiac arrest. The method includes the step of administering an effective amount of a gliflozin solution to the human subject concurrent with cardiac resuscitation. The gliflozin is suspended or dissolved in a diluent at an appropriate concentration and the solution is delivered to the human patient by intravenous injection or intraosseous injection. In one preferred form of the invention, the gliflozin is EMPA. Other suitable gliflozins include canagliflozin and dapagliflozin, and others known to those having ordinary skill in the art.

Suitable interventions for cardiopulmonary resuscitation include mechanical, electrical, and chemical interventions, often given in combination. The cardiopulmonary resuscitation can be closed-chest or open-chest. The gliflozin can be administered by a route including intravenous and intraosseous. The administration of the gliflozin is in bolus and can be followed by continuous infusion. Preferably, the gliflozin is administered during the cardiopulmonary resuscitation, that is during the mechanical resuscitation, during the electrical resuscitation, or during both the mechanical and electrical resuscitation efforts.

The gliflozin can be administered by a route including intravenous and intraosseous. The administration of the gliflozin is in bolus and can be followed by continuous infusion.

The cardiac arrest can be due to ventricular fibrillation, pulseless ventricular tachycardia, pulseless electrical activity, or asystole.

The present invention further provides a kit for administering gliflozin solution to a human patient in cardiac arrest during cardiopulmonary resuscitation. The kit includes a pre-filled syringe and the corresponding packing with an effective amount of a gliflozin ready for delivery to a human patient in cardiac arrest. The gliflozin solution contained in the pre-filled syringe is ready for immediate delivery to a human subject by intravenous or intraosseous injection. The gliflozin solution can also be contained in a flexible plastic, IV bag with a tubing set terminated with an access device for continuous intravenous or intraosseous delivery. The kit can also include a prefilled syringe for a bolus injection of gliflozin and an IV bag containing a gliflozin solution for continuous parenteral infusion to the patient. The kit can also include a set of instructions for how to administer the gliflozin.

REFERENCES

1. Zinman B, Wanner C, Lachin J M, Fitchett D, Bluhmki E, Hantel S, Mattheus M, Devins T, Johansen O E, Woerle H J, Broedl U C, Inzucchi S E. Empagliflozin, Cardiovascular Outcomes, and Mortality in Type 2 Diabetes. *N Engl J Med* 2015; 373:2117-28.
2. Andreadou I, Efentakis P, Balafas E, Togliatto G, Davos C H, Varela A, Dimitriou C A, Nikolaou P E, Maratou E, Lambadiari V, Ikonomidis I, Kostomitsopoulos N, Brizzi M F, Dimitriadis G, Iliodromitis E K. Empagliflozin Limits Myocardial Infarction in Vivo and Cell Death in Vitro: Role of STAT3, Mitochondria, and Redox Aspects. *Front Physiol* 2017; % 19; 8:1077. doi: 10.3389/fphys.2017.01077. eCollection; %2017.:1077.
3. Neal B, Perkovic V, Mahaffey K W, de Z D, Fulcher G, Erondu N, Shaw W, Law G, Desai M, Matthews D R. Canagliflozin and Cardiovascular and Renal Events in Type 2 Diabetes. *N Engl J Med* 2017; 377:644-57.

4. Lim V G, Bell R M, Arjun S, Kolatsi-Joannou M, Long D A, Yellon D M. SGLT2 Inhibitor, Canagliflozin, Attenuates Myocardial Infarction in the Diabetic and Nondiabetic Heart. *JACC Basic Transl Sci* 2019; 4:15-26.
5. Santos-Gallego C G, Garcia-Ropero A, Mancini D, Pinney S P, Contreras J P, Fergus I, Abascal V, Moreno P, Atallah-Lajam F, Tamler R, Lala A, Sanz J, Fuster V, Badimon J J. Rationale and Design of the EMPA-TROPISM Trial (ATRU-4): Are the "Cardiac Benefits" of Empagliflozin Independent of its Hypoglycemic Activity? *Cardiovasc Drugs Ther* 2019; 33:87-95.
6. Baartscheer A, Schumacher C A, Wust R C I, Fiolet J W, Stienen G J, Coronel R, Zuurbier C J. Empagliflozin decreases myocardial cytoplasmic Na(+) through inhibition of the cardiac Na(+)/H(+) exchanger in rats and rabbits. *Diabetologia* 2017; 60:568-73.
7. Uthman L, Baartscheer A, Bleijlevens B, Schumacher C A, Fiolet J W T, Koeman A, Jancev M, Hollmann M W, Weber N C, Coronel R, Zuurbier C J. Class effects of SGLT2 inhibitors in mouse cardiomyocytes and hearts: inhibition of Na(+)/H(+) exchanger, lowering of cytosolic Na(+) and vasodilation. *Diabetologia* 2018; 61:722-6.
8. Pedersen S F, King S A, Nygaard E B, Rigor R R, Cala P M. NHE1 inhibition by amiloride- and benzoylguanidine-type compounds. Inhibitor binding loci deduced from chimeras of NHE1 homologues with endogenous differences in inhibitor sensitivity. *J Biol Chem* 2007; 282:19716-27.
9. Gazmuri R J, Radhakrishnan J, Ayoub I M. Sodium-Hydrogen Exchanger Isoform-1 Inhibition: A Promising Pharmacological Intervention for Resuscitation from Cardiac Arrest. *Molecules* 2019; 24:molecules24091765.
10. Ayoub I M, Kolarova J D, Yi Z, Trevedi A, Deshmukh H, Lubell D L, Franz M R, Maldonado F A, Gazmuri R J. Sodium-hydrogen exchange inhibition during ventricular fibrillation: Beneficial effects on ischemic contracture, action potential duration, reperfusion arrhythmias, myocardial function, and resuscitability. *Circulation* 2003; 107:1804-9.
11. Baker H E, Kiel A M, Luebbe S T, Simon B R, Earl C C, Regmi A, Roell W C, Mather K J, Tune J D, Goodwill A G. Inhibition of sodium-glucose cotransporter-2 preserves cardiac function during regional myocardial ischemia independent of alterations in myocardial substrate utilization. *Basic Res Cardiol* 2019;%19; 114:25-0733.
12. Sayour A A, Korkmaz-Icoz S, Loganathan S, Ruppert M, Sayour V N, Olah A, Benke K, Brune M, Benko R, Horvath E M, Karck M, Merkely B, Radovits T, Szabo G. Acute canagliflozin treatment protects against in vivo myocardial ischemia-reperfusion injury in non-diabetic male rats and enhances endothelium-dependent vasorelaxation. *J Transl Med* 2019; 17:127-1881.
13. Ayoub I M, Kolarova J, Kantola R, Radhakrishnan J, Gazmuri R J. Zoniporide preserves left ventricular compliance during ventricular fibrillation and minimizes postresuscitation myocardial dysfunction through benefits on energy metabolism. *Crit Care Med* 2007; 35:2329-36.
14. Borovnik-Lesjak V, Whitehouse K, Baetiong A, Artin B, Radhakrishnan J, Gazmuri R J. High-dose erythropoietin during cardiac resuscitation lessens postresuscitation myocardial stunning in swine. *Transl Res* 2013; 162:110-21.
15. McGovern T G. Tertiary Pharmacology/Toxicology Review: Empagliflozin. *DEPARTMENT OF HEALTH & HUMAN SERVICES: Food and Drug Administration;* 2013.
16. Scheen A J. Pharmacokinetic and pharmacodynamic profile of empagliflozin, a sodium glucose co-transporter 2 inhibitor. *Clin Pharmacokinet* 2014; 53:213-25.
17. Chen L, Mao Y, Sharp D E, Schadt S, Pagels S, Press R, Cheng T, Potchoiba M J, Collins W. Pharmacokinetics, Biotransformation, Distribution and Excretion of Empagliflozin, a Sodium-Glucose Co-Transporter (SGLT 2) Inhibitor, in Mice, Rats, and Dogs. *J Pharm Drug Devel* 2015; 3:302.
18. Uthman L, Nederlof R, Eerbeek O, Baartscheer A, Schumacher C, Buchholtz N, Hollmann M W, Coronel R, Weber N C, Zuurbier C J. Delayed ischemic contracture onset by Empagliflozin associates with NHE-1 inhibition and is dependent on insulin in isolated mouse hearts. *Cardiovasc Res* 2019; 5288517.
19. Pabel S, Wagner S, Bollenberg H, Bengel P, Kovács Á, Schach C, Tirilomis P, Mustroph J, Renner A, Gummert J, Fischer T, Van L S, Tschöpe C, Streckfuss-Bömeke K, Hasenfuss G, Maier L S, Hamdani N, Sossalla S. Empagliflozin directly improves diastolic function in human heart failure. *Eur J Heart Fail* 2018; 20:1690-700.
20. Bellamy R F, DeGuzman L R, Pedersen DC. Coronary blood flow during cardiopulmonary resuscitation in swine. *Circulation* 1984; 69:174-80.
21. Schwarz B, Bowdle T A, Jett G K, Mair P, Lindner K H, Aldea G S, Lazzara R G, O'Grady S G, Schmitt P W, Walker R G, Chapman F W, Tacker W A. Biphasic shocks compared with monophasic damped sine wave shocks for direct ventricular defibrillation during open heart surgery. *Anesthesiology* 2003; 98:1063-9.
22. Kelley K W, Curtis S E, Marzan G T, Karara H M, Anderson C R. Body surface area of female swine. *J Anim Sci* 1973; 36:927-30.
23. Kolarova J, Ayoub I M, Yi Z, Gazmuri R J. Optimal timing for electrical defibrillation after prolonged untreated ventricular fibrillation. *Crit Care Med* 2003; 31:2022-8.
24. Aiello S, Perez M, Cogan C, Baetiong A, Miller S A, Radhakrishnan J, Kaufman C L, Gazmuri R J. Real-Time Ventricular Fibrillation Amplitude-Spectral Area Analysis to Guide Timing of Shock Delivery Improves Defibrillation Efficacy During Cardiopulmonary Resuscitation in Swine. *J Am Heart Assoc* 2017; 6.
25. Perkins G D, Ji C, Deakin C D, Quinn T, Nolan J P, Scomparin C, Regan S, Long J, Slowther A, Pocock H, Black J J M, Moore F, Fothergill R T, Rees N, O'Shea L, Docherty M, Gunson I, Han K, Charlton K, Finn J, Petrou S, Stallard N, Gates S, Lall R. A Randomized Trial of Epinephrine in Out-of-Hospital Cardiac Arrest. *N Engl J Med* 2018; 379:711-21.
26. Gazmuri R J, Aiello S. Epinephrine in Out-of-Hospital Cardiac Arrest. *N Engl J Med* 2019; 380:394-5.
27. Brucken A, Derwall M, Bleilevens C, Stoppe C, Gotzenich A, Gaisa N T, Weis J, Nolte K W, Rossaint R, Ichinose F, Fries M. Brief inhalation of nitric oxide increases resuscitation success and improves 7-day-survival after cardiac arrest in rats: a randomized controlled animal study. *Crit Care* 2015; 19:408. doi: 10.1186/s13054-015-1128-x.:408-1128.
28. Derwall M, Ebeling A, Nolte K W, Weis J, Rossaint R, Ichinose F, Nix C, Fries M, Brucken A. Inhaled nitric oxide improves transpulmonary blood flow and clinical outcomes after prolonged cardiac arrest: a large animal study. *Crit Care* 2015; 19:328-1050.
29. Di Franco A., Cantini G, Tani A, Coppini R, Zecchi-Orlandini S, Raimondi L, Luconi M, Mannucci E. Sodium-dependent glucose transporters (SGLT) in human ischemic heart: A new potential pharmacological target. *Int J Cardiol* 2017; 243:86-90. doi: 10.1016/j.ijcard.2017.05.032. Epub; %2017 May 9.:86-90.
30. Radhakrishnan J, Wang S, Ayoub I M, Kolarova J D, Levine R F, Gazmuri R J. Circulating levels of cytochrome c after resuscitation from cardiac arrest: a marker of mitochondrial injury and predictor of survival. *Am J Physiol Heart Circ Physiol* 2007; 292:H767-H775.
31. Wang S, Radhakrishnan J, Ayoub I M, Kolarova J D, Taglieri D M, Gazmuri R J. Limiting sarcolemmal Na+ entry during resuscitation from VF prevents excess mitochondrial Ca2+ accumulation and attenuates myocardial injury. *J Appl Physiol* 2007; 103:55-65.
32. Baker H E. Inhibition of Sodium Glucose Cotransporter-2 Improves Cardiac Efficiency During Regional Myocardial Ischemia Independent of Sodium/Hydrogen Exchanger-1. In: *Mechanisms Underlying Cardiovascular Benefits of Sodium Glucose Co-Transporter-2 Inhibitors: Myocardial Substrate or Sodium/Hydrogen Exchanger?* Vol Dissertation. Cellular & Integrative Physiology, Indiana University; 2020.
33. Mustroph J, Wagemann O, Lucht C M, Trum M, Hammer K P, Sag C M, Lebek S, Tarnowski D, Reinders J, Perbellini F, Terracciano C, Schmid C, Schopka S, Hilker M, Zausig Y, Pabel S, Sossalla S T, Schweda F, Maier L S, Wagner S. Empagliflozin reduces Ca/calmodulin-dependent kinase II activity in isolated ventricular cardiomyocytes. *ESC Heart Fail* 2018; 5:642-8.
34. Cappetta D, De A A, Ciuffreda L P, Coppini R, Cozzolino A, Micciche A, Dell'Aversana C, D'Amario D, Cianflone E, Scavone C, Santini L, Palandri C, Naviglio S, Crea F, Rota M, Altucci L, Rossi F, Capuano A, Urbanek K, Berrino L. Amelioration of diastolic dysfunction by dapagliflozin in a non-diabetic model involves coronary endothelium. *Pharmacol Res* 2020; 157:104781. doi: 10.1016/j.phrs.2020.104781. Epub; %2020 Apr. 28.: 104781.

Many modifications and variations of the present invention are possible in light of the above teachings. It is, therefore, to be understood within the scope of the appended claims the invention may be protected otherwise than as specifically described.

We claim:

1. A method of cardiopulmonary resuscitation on a mammalian subject comprising administering an effective amount of a gliflozin solution to the subject concurrent with cardiac resuscitation.

2. The method of claim 1 wherein the gliflozin is empagliflozin.

3. The method of claim 1 wherein the mammalian subject is human.

4. The method of claim 1 wherein the cardiac resuscitation is mechanical, electrical, chemical, or a combination thereof.

5. The method of claim 1 wherein the cardiopulmonary resuscitation is closed-chest or open-chest.

6. The method of claim 1 wherein the gliflozin is administered by a route selected from the group consisting of intravenous or intraosseous.

7. The method of claim 1 wherein the administration of the gliflozin is in bolus.

8. The method of claim 7 further comprising administering gliflozin continuously through parenteral infusion.

9. The method of claim 8 wherein the bolus injection is performed first followed by the step of parenteral infusion.

10. The method of claim 1 wherein the cardiac arrest is due to ventricular fibrillation, pulseless ventricular tachycardia, pulseless electrical activity, or asystole.

* * * * *